(12) United States Patent
Haynes et al.

(10) Patent No.: US 10,920,288 B2
(45) Date of Patent: Feb. 16, 2021

(54) DETECTION OF PARTICLE-CONTAINED REVERSE TRANSCRIPTASE ACTIVITY

(71) Applicant: TAKEDA VACCINES, INC., Cambridge, MA (US)

(72) Inventors: Joel R. Haynes, Bozeman, MT (US); Evelyn Benson, Bozeman, MT (US)

(73) Assignee: Takeda Vaccines, Inc., Cambridge, MA (US)

( * ) Notice: Subject to any disclaimer, the term of this patent is extended or adjusted under 35 U.S.C. 154(b) by 0 days.

(21) Appl. No.: 15/542,265

(22) PCT Filed: Jan. 15, 2016

(86) PCT No.: PCT/US2016/013641
§ 371 (c)(1),
(2) Date: Jul. 7, 2017

(87) PCT Pub. No.: WO2016/115484
PCT Pub. Date: Jul. 21, 2016

(65) Prior Publication Data
US 2018/0002767 A1   Jan. 4, 2018

Related U.S. Application Data

(60) Provisional application No. 62/104,252, filed on Jan. 16, 2015.

(51) Int. Cl.
| | | |
|---|---|---|
| C12Q 1/70 | (2006.01) | |
| C12N 9/12 | (2006.01) | |
| C12N 7/02 | (2006.01) | |
| C12Q 1/6806 | (2018.01) | |
| C12N 7/00 | (2006.01) | |

(52) U.S. Cl.
CPC ............... *C12Q 1/702* (2013.01); *C12N 7/00* (2013.01); *C12N 7/02* (2013.01); *C12N 9/1276* (2013.01); *C12Q 1/6806* (2013.01); *C12Q 1/70* (2013.01); *C12Q 1/701* (2013.01); *C12Y 207/07049* (2013.01); *C12Y 304/21062* (2013.01); *C12N 2740/00011* (2013.01); *C12N 2740/10023* (2013.01)

(58) Field of Classification Search
CPC ................... C12Q 1/702; C12Y 207/07049
See application file for complete search history.

(56) References Cited

U.S. PATENT DOCUMENTS

| | | |
|---|---|---|
| 6,670,116 B2 | 12/2003 | Zimmermann et al. |
| 2007/0092534 A1* | 4/2007 | Whitehead ........... A61K 39/295 424/204.1 |
| 2012/0219576 A1 | 8/2012 | Branco et al. |
| 2014/0322255 A1 | 10/2014 | Feederle et al. |

FOREIGN PATENT DOCUMENTS

| | | |
|---|---|---|
| WO | WO 1998/049351 A1 | 11/1998 |
| WO | WO 2001/027318 A2 | 4/2001 |
| WO | WO 2002/082088 A1 | 10/2002 |
| WO | WO 2006/088601 A2 | 8/2006 |
| WO | WO 2013/098364 A1 | 7/2013 |
| WO | WO 2013/192604 A1 | 12/2013 |
| WO | WO 2014/055746 A1 | 4/2014 |
| WO | WO 2015/051255 A1 | 4/2015 |
| WO | WO 2016/115484 A1 | 7/2016 |

OTHER PUBLICATIONS

Wolf JJ, Wang L, Wang F. Application of PCR technology in vaccine product development. Expert Rev Vaccines. Aug. 2007; 6(4): 547-58. (Year: 2007).*
Andre M, Morgeaux S, Fuchs F. Quantitative detection of RT activity by PERT assay: feasibility and limits to a standardized screening assay for human vaccines. Biologicals. Jun. 2000; 28(2):67-80. (Year: 2000).*
Pyra H, Böni J, Schüpbach J. Ultrasensitive retrovirus detection by a reverse transcriptase assay based on product enhancement. Proc Natl Acad Sci U S A. Feb. 15, 1994; 91(4):1544-8. (Year: 1994).*
Chang A, Ostrove JM, Bird RE. Development of an improvement product enhanced reverse transcriptase assay. J Virol Methods 1997; 65: 45-54. (Year: 1997).*
Nuanualsuwan S, Oliver DO. Pretreatment to avoid positive RT-PCR results with inactivated viruses. J Virol Methods. Jul. 2002; 104 (2):217-25. (Year: 2002).*
Durbin et al. Attenuation and immunogenicity in humans of a live dengue virus type-4 vaccine candidate with a30 nucleotide deletion in its 3'-untranslated region. Am J Trop Med Hyg. Nov. 2001: 65(5):405-13. (Year: 2001).*
Pfaender S, Brinkmann J, Todt D, Riebesehl N, Steinmann J, Steinmann J, Pietschmann T, Steinmann E. Mechanisms of methods for hepatitis C virus inactivation. Appl Environ Microbiol. Mar. 2015; 81(5):1616-21. Epub Dec. 19, 2014. (Year: 2014).*
Database Geneseq [Online], "Dengue virus PCR primer #9." Database accession No. AAV73967, retrieved from EBI accession No. GSN:AAV73967, Mar. 5, 1999, 1 page.
Database Geneseq [Online], "Dengue virus type 4 DNA, SEQ ID 4." Database accession No. BBF27655, retrieved from EBI accession No. GSN:BBF27655, Jun. 5, 2014, 3 pages.
European Patent Application No. 16737978.3, Extended European Search Report dated Aug. 3, 2018, 10 pages.
Kaczmarczyk, et al., "Protein delivery using engineered virus-like particles." Proc Natl Acad Sci U S A. (2011); 108 (41): 16998-17003. Epub Sep. 26, 2011.
International Application No. PCT/US2016/013641, International Preliminary Report on Patentability dated Jul. 18, 2017, 7 pages.

(Continued)

*Primary Examiner* — Teresa E Strzelecka
*Assistant Examiner* — Olayinka A Oyeyemi
(74) *Attorney, Agent, or Firm* — Cooley LLP

(57) ABSTRACT

The present invention relates to methods and kits for detecting in a sample the presence of a virus particle or a virus-like particle that has reverse transcriptase activity and methods for preparing a retroviral contaminant-free substance. An aspect of the present invention is a method for detecting the presence of a virus particle in a sample of a Virus-like Particle (VLP) drug substance comprising a step of performing PCR-based reverse transcriptase (PBRT) on a sample of the VLP drug substance that has been treated with a protease.

19 Claims, No Drawings

Specification includes a Sequence Listing.

(56) References Cited

OTHER PUBLICATIONS

International Application No. PCT/US2016/013641, International Search Report and Written Opinion, dated Apr. 1, 2016, 11 pages.

Pfaender, et al., "Mechanisms of Methods for Hepatitis C Virus Inactivation." Applied and Environmental Microbiology (2015); 81(5): 1616-1621 [published on-line Dec. 19, 2014].

Wisher, M., "Biosafety and product release testing issues relevant to replication-competent oncolytic viruses." Cancer Gene Therapy (2002); 9: 1056-1061.

Fassati and Goff, "Characterization of Intracellular Reverse Transcription Complexes of Moloney Murine Leukemia Virus". Journal of Virology (Nov. 1999); 73(11): 8919-8925.

Ferris, et al., "Immunologic and Proteolytic Analysis of HIV-1 Reverse Transcriptase Structure". Virology (1990); 175(2): 456-464.

Öhagen and Gabuzda, "Role of Vif in Stability of the Human Immunodeficiency Virus Type 1 Core". Journal of Virology (Dec. 2000); 74(23): 11055-11066.

[Author Unknown] Cervarix clinical trial result report, Pharmaceuticals and Medical Devices Agency, Clinical trial result report, Sep. 8, 2009, with English translation, 173 pages, http://www.pmda.go.jp/drugs/2009/P200900052/34027800_22100AMX022868_A100_1.pdf.

López-Macías, Constantino, "Virus-like particle (VLP)-based vaccines for pandemic influenza. Performance of a VLP vaccine during the 2009 influenza pandemic". Journal Human Vaccines & Immunotherapeutics (Mar. 2012); 8(3): 411-414. Epub Feb. 14, 2012.

Roldão, et al., "Virus-like particles in vaccine development". Expert Review of Vaccines (Oct. 2010); 9(10): 1149-1176.

\* cited by examiner

SEQUENCE LISTING

```
<160> NUMBER OF SEQ ID NOS: 5

<210> SEQ ID NO 1
<211> LENGTH: 10649
<212> TYPE: DNA
<213> ORGANISM: Dengue virus type 4 strain 814669

<400> SEQUENCE: 1
agttgttagt ctgtgtggac cgacaaggac agttccaaat cggaagcttg cttaacacag      60
ttctaacagt ttgtttgaat agagagcaga tctctggaaa aatgaaccaa cgaaaaaagg     120
tggttagacc acctttcaat atgctgaaac gcgagagaaa ccgcgtatca acccctcaag     180
ggttggtgaa gagattctca accggacttt tttctgggaa aggacccctta cggatggtgc     240 tagcattcat cacgttttg cgagtccttt ccatcccacc aacagcaggg attctgaaga     300
gatggggaca gttgaagaaa aataaggcca tcaagatact gattggattc aggaaggaga     360
taggccgcat gctgaacatc ttgaacggga gaaaaaggtc aacgataaca ttgctgtgct     420
tgattcccac cgtaatggcg ttttccttgt caacaagaga tggcgaaccc ctcatgatag     480
tggcaaaaca tgaaaggggg agacctctct tgtttaagac aacagagggg atcaacaaat     540
gcactctcat tgccatggac ttgggtgaaa tgtgtgagga cactgtcacg tataaatgcc     600
ccctactggt caataccgaa cctgaagaca ttgattgctg gtgcaacctc acgtctacct     660
gggtcatgta tgggacatgc acccagagcg gagaacggag acgagagaag cgctcagtag     720
ctttaacacc acattcagga atgggattgg aaacaagagc tgagacatgg atgtcatcgg     780
aaggggcttg gaagcatgct cagagagtag agagctggat actcagaaac ccaggattcg     840
cgctcttggc aggatttatg gcttatatga ttgggcaaac aggaatccag cgaactgtct     900
tctttgtcct aatgatgctg gtcgccccat cctacggaat gcgatgcgta ggagtaggaa     960
acagagactt tgtggaagga gtctcaggtg gagcatgggt cgacctggtg ctagaacatg    1020
gaggatgcgt cacaaccatg gcccagggaa aaccaacctt ggattttgaa ctgactaaga    1080
caacagccaa ggaagtggct ctgttaagaa cctattgcat tgaagcctca atatcaaaca    1140
taactacggc aacaagatgt ccaacgcaag gagagcctta tctgaaagag gaacaggacc    1200
aacagtacat ttgccggaga gatgtggtag acagagggtg gggcaatggc tgtggcttgt    1260
ttggaaaagg aggagttgtg acatgtgcga gttttcatg ttcggggaag ataacaggca    1320
atttggtcca aattgagaac cttgaataca cagtggttgt aacagtccac aatggagaca    1380
cccatgcagt aggaaatgac acatccaatc atggagttac agccatgata actcccaggt    1440
```

```
caccatcggt ggaagtcaaa ttgccggact atggagaact aacactcgat tgtgaaccca    1500
ggtctggaat tgactttaat gagatgattc tgatgaaaat gaaaagaaa acatggctcg     1560 tgcataagca atggtttttg gatctgcctc ttccatggac agcaggagca gacacatcag    1620
aggttcactg gaattacaaa gagagaatgg tgacatttaa ggttcctcat gccaagagac    1680
aggatgtgac agtgctggga tctcaggaag gagccatgca ttctgccctc gctggagcca    1740
cagaagtgga ctccggtgat ggaaatcaca tgtttgcagg acatcttaag tgcaaagtcc    1800
gtatggagaa attgagaatc aagggaatgt catacacgat gtgttcagga aagttttcaa    1860
ttgacaaaga gatggcagaa acacagcatg gacaacagt ggtgaaagtc aagtatgaag     1920
gtgctggagc tccgtgtaaa gtccccatag agataagaga tgtaaacaag gaaaaagtgg    1980
ttgggcgtat catctcatcc acccctttgg ctgagaatac caacagtgta accaacatag    2040
aattagaacc ccccttgggg gacagctaca tagtgatagg tgttggaaac agcgcattaa    2100
cactccattg gttcaggaaa gggagttcca ttggcaagat gtttgagtcc acatacagag    2160
gtgcaaaacg aatggccatt ctaggtgaaa cagcttggga ttttggttcc gttggtggac    2220
tgttcacatc attgggaaag gctgtgcacc aggttttttgg aagtgtgtat acaaccatgt    2280
ttggaggagt ctcatggatg attagaatcc taattgggtt cttagtgttg tggattggca    2340
cgaactcaag gaacacttca atggctatga cgtgcatagc tgttggagga atcactctgt    2400
ttctgggctt cacagttcaa gcagacatgg gttgtgtggt gtcatggagt gggaaagaat    2460
tgaagtgtgg aagcggaatt tttgtggttg acaacgtgca cacttggaca gaacagtaca    2520
aatttcaacc agagtcccca gcgagactag cgtctgcaat attaaatgcc acaaagatg     2580 gggtctgtgg aattagatca accacgaggc tggaaaatgt catgtggaag caaataacca    2640
acgagctaaa ctatgttctc tgggaaggag acatgacct cactgtagtg gctggggatg     2700 tgaaggggt gttgaccaaa ggcaagagag cactcacacc cccagtgagt gatctgaaat     2760
attcatggaa gacatgggga aaagcaaaaa tcttcacccc agaagcaaga aatagcacat    2820
ttttaataga cggaccagac acctctgaat gccccaatga acgaagagca tggaactctc    2880
ttgaggtgga agactatgga tttggcatgt tcacgaccaa catatggatg aaattccgag    2940
aaggaagttc agaagtgtgt gaccacaggt taatgtcagc tgcaattaaa gatcagaaag    3000
ctgtgcatgc tgacatgggt tattggatag agagctcaaa aaaccagacc tggcagatag    3060
agaaagcatc tcttattgaa gtgaaaacat gtctgtggcc caagacccac acactgtgga    3120
gcaatggagt gctggaaagc cagatgctca ttccaaaatc atatgcgggc cctttttcac    3180
agcacaatta ccgccagggc tatgccacgc aaaccgtggg cccatggcac ttaggcaaat    3240
tagagataga cttttgagaa tgccccggaa caacagtcac aattcaggag gattgtgacc    3300
atagaggccc atctttgagg accaccactg catctggaaa actagtcacg caatggtgct    3360
gccgctcctg cacgatgcct cccttaaggt tcttgggaga agatgggtgc tggtatggga    3420
tggagattag gcccttgagt gaaaaagaag agaacatggt caaatcacag gtgacggccg    3480
gacagggcac atcagaaact ttttctatgg gtctgttgtg cctgaccttg tttgtggaag    3540
aatgcttgag gagaagagtc actaggaaac acatgatatt agttgtggtg atcactcttt    3600
gtgctatcat cctgggaggc ctcacatgga tggacttact acgagccctc atcatgttgg    3660
gggacactat gtctggtaga ataggaggac agatccacct agccatcatg gcagtgttca    3720
agatgtcacc aggatacgtg ctgggtgtgt ttttaaggaa actcacttca agagagacag    3780
cactaatggt aataggaatg gccatgacaa cggtgctttc aattccacat gaccttatgg    3840
```

-continued

```
aactcattga tggaatatca ctgggactaa ttttgctaaa aatagtaaca cagtttgaca      3900
acacccaagt gggaacctta gctctttcct tgactttcat aagatcaaca atgccattgg      3960
tcatggcttg gaggaccatt atggctgtgt tgtttgtggt cacactcatt cctttgtgca      4020
ggacaagctg tcttcaaaaa cagtctcatt gggtagaaat aacagcactc atcctaggag      4080
cccaagctct gccagtgtac ctaatgactc ttatgaaagg agcctcaaga agatcttggc      4140
ctcttaacga gggcataatg gctgtgggtt tagttagtct cttaggaagc gctcttttaa      4200
agaatgatgt cccctttagct ggcccaatgg tggcaggagg cttacttctg gcggcttacg     4260
tgatgagtgg tagctcagca gatctgtcac tagagaaggc cgccaatgtg cagtgggatg      4320
aaatggcaga cataacaggc tcaagcccaa tcatagaagt gaagcaggat gaagatggct      4380 cttctctccat acgggacgtc gaggaaacca atatgataac ccttttggtg aaactggcac      4440
tgataacagt gtcaggtctc tacccctttgg caattccagt cacaatgacc ttatggtaca      4500
tgtggcaagt gaaaacacaa agatcaggag ccctgtggga cgtcccctca cccgctgcca      4560
ctaaaaaagc cgcactgtct gaaggagtgt acaggatcat gcaaagaggg ttattcggga      4620
aaactcaggt tggagtaggg atacacatgg aaggtgtatt tcacacaatg tggcatgtaa      4680
caagaggatc agtgatctgc cacgagactg ggagattgga gccatcttgg gctgacgtca      4740
ggaatgacat gatatcatac ggtgggggat ggaggcttgg agacaaatgg gacaaagaag      4800
aagacgttca ggtcctcgcc atagaaccag gaaaaaatcc taaacatgtc caaacgaaac      4860
ctggcctttt caagacccta actggagaaa ttggagcagt aacattagat ttcaaacccg      4920
gaacgtctgg ttctcccatc atcaacagga aggaaaagt catcggactc tatggaaatg      4980
gagtagttac caaatcaggt gattacgtca gtgccataac gcaagccgaa agaattggag      5040
agccagatta tgaagtggat gaggacattt ttcgaaagaa aagattaact ataatggact      5100
tacaccccgg agctggaaag acaaaaagaa ttcttccatc aatagtgaga gaagccttaa      5160
aaaggaggct acgaacttg atttttagctc ccacgagagt ggtggcggcc gagatggaag      5220
aggccctacg tggactgcca atccgttatc agaccccagc tgtgaaatca gaacacacag      5280
gaagagagat tgtagacctc atgtgtcatg caaccttcac aacaagactt ttgtcatcaa      5340
ccagggttcc aaattacaac cttatagtga tggatgaagc acatttcacc gatccttcta      5400
gtgtcgcggc tagaggatac atctcgacca gggtggaaat gggagaggca gcagccatct      5460
tcatgaccgc aacccctccc ggagcgacag atccctttcc ccagagcaac agcccaatag      5520
aagacatcga gagggaaatt ccggaaaggt catggaacac agggttcgac tggataacag      5580
actaccaagg gaaaactgtg tggtttgttc ccagcataaa agctggaaat gacattgcaa      5640
attgtttgag aaagtcggga aagaaagtta tccagttgag taggaaaacc tttgatacag      5700
agtatccaaa aacgaaactc acggactggg actttgtggt cactacagac atatctgaaa      5760
tgggggccaa ttttagagcc gggagagtga tagaccctag aagatgcctc aagccagtta      5820
tcctaacaga tgggccagag agagtcattt tagcaggtcc tattccagtg actccagcaa      5880
gcgctgctca gagaagaggg cgaataggaa ggaacccagc acaagaagac gaccaatacg      5940 ttttctcgg agacccacta aaaaatgatg aagatcatgc ccactggaca gaagcaaaga      6000
tgctgcttga caatatctac acccccagaag ggatcattcc aacattgttt ggtccggaaa      6060
gggaaaaaac ccaagccatt gatggagagt ttcgcctcag agggggaacaa aggaagactt      6120 ttgtggaatt aatgaggaga ggagaccttc cggtgtggct gagctataag gtagcttctg      6180
ctggcatttc ttacaaagat cgggaatggt gcttcacagg ggaaagaaat aaccaaattt      6240
```

```
tagaagaaaa catggaggtt gaaatttgga ctagagaggg agaaaagaaa aagctaaggc      6300
caagatggtt agatgcacgt gtatacgctg accccatggc tttgaaggat ttcaaggagt      6360
ttgccagtgg aaggaagagt ataactctcg acatcctaac agagattgcc agtttgccaa      6420
cttacctttc ctctagggcc aagctcgccc ttgataacat agtcatgctc cacacaacag      6480
aaagaggagg gagggcctat caacacgccc tgaacgaact tccggagtca ctggaaacac      6540
tcatgcttgt agctttacta ggtgctatga cagcaggcat cttcctgttt ttcatgcaag      6600
ggaaaggaat agggaaattg tcaatgggtt tgataaccat tgcggtggct agtggcttgc      6660
tctgggtagc agaaattcaa ccccagtgga tagcggcctc aatcatacta gagttttttc      6720
tcatggtact gttgataccg gaaccagaaa aacaaaggac cccacaagac aatcaattga      6780
tctacgtcat attgaccatt ctcaccatca ttggtctaat agcagccaac agatgggggc      6840
tgattgaaaa aacaaaaacg gattttgggt tttaccaggt aaaaacagaa accaccatcc      6900
tcgatgtgga cttgagacca gcttcagcat ggacgctcta tgcagtagcc accacaattc      6960
tgactcccat gctgagacac accatagaaa acacgtcggc caacctatct ctagcagcca      7020
ttgccaacca ggcagccgtc ctaatggggc ttgaaaaagg atggccgctc cacagaatgg      7080
acctcggtgt gccgctgtta gcaatgggat gctattctca agtgaaccca acaaccttga      7140
cagcatcctt agtcatgctt ttagtccatt atgcaataat aggcccagga ttgcaggcaa      7200
aagccacaag agaggcccag aaaaggacag ctgctgggat catgaaaaat ccacagtgg      7260 acgggataac agtaatagat ctagaaccaa tatcctatga cccaaaattt gaaaagcaat      7320
tagggcaggt catgctacta gtcttgtgtg ctggacaact actcttgatg agaacaacat      7380 gggcttttctg tgaagtcttg actttggcca caggaccaat cttgaccttg tgggagggca      7440
acccgggaag gttttggaac acgaccatag ccgtatccac cgccaacatt tcaggggaa      7500 gttacttggc gggagctgga ctggctttt cactcataaa gaatgcacaa cccctagga      7560 ggggaactgg gaccacagga gagacactgg agagaagtg aagagacag ctaaactcat      7620 tagacagaag agagtttgaa gagtataaaa gaagtggaat actagaagtg gacaggactg      7680
aagccaagtc tgccctgaaa gatgggtcta aaatcaagca tgcagtatct agagggtcca      7740
gtaagatcag atggattgtt gagagaggga tggtaaagcc aaaagggaaa gttgtagatc      7800
ttggctgtgg agaggaggag tggtcttatt acatggcgac actcaagaac gtgactgaag      7860
tgaaagggta tacaaaagga ggtccaggac atgaagaacc gattcccatg gctacttatg      7920 gttgaatt tggtcaaactc cattcagggg ttgacgtgtt ctacaaaccc acagagcaag      7980
tggacaccct gctctgtgat attggggagt catcttctaa tccaacaata gaggaaggaa      8040
gaacattaag agttttgaag atggtggagc catggctctc ttcaaaacct gaattctgca      8100
tcaaagtcct taacccctac atgccaacag tcatagaaga gctggagaaa ctgcagagaa      8160
aacatggtgg gaaccttgtc agatgcccgc tgtccaggaa ctccacccat gagatgtatt      8220
gggtgtcagg agcgtcggga acattgtga gctctgtgaa cacaacatca aagatgttgt      8280
tgaacaggtt cacaacaagg cataggaaac ccacttatga aaggacgta gatcttgggg      8340 caggaacgag aagtgtctcc actgaaacag aaaaaccaga catgacaatc attgggaga      8400 ggcttcagcg attgcaagaa gagcacaaag aaacctggca ttatgatcag gaaaacccat      8460
acagaacctg ggcgtatcat ggaagctatg aagctccttc gacaggctct gcatcctcca      8520
tggtgaacgg ggtagtaaaa ctgctaacaa accctgggga tgtgattcca atggtgactc      8580
agttagccat gacagataca accccttttg ggcaacaaag agtgttcaaa gagaaggtgg      8640
```

```
ataccagaac accacaacca aaacccggta cacgaatggt tatgaccacg acagccaatt    8700
ggctgtgggc cctccttgga aagaagaaaa atcccagact gtgcacaagg gaagagttca    8760
tctcaaaagt tagatcaaac gcagccatag gcgcagtctt tcaggaagaa cagggatgga    8820
catcagccag tgaagctgtg aatgacagcc ggttttggga actggttgac aaagaaaggg    8880
ccctacacca ggaagggaaa tgtgaatcgt gtgtctataa catgatggga aaacgtgaga    8940
aaaagttagg agagtttggc agagccaagg gaagccgagc aatctggtac atgtggctgg    9000
gagcgcggtt tctggaattt gaagccctgg gttttttgaa tgaagatcac tggtttggca    9060
gagaaaattc atggagtgga gtggaagggg aaggtctgca cagattggga tatatcctgg    9120
aggagataga caagaaggat ggagacctaa tgtatgctga tgacacagca ggctgggaca    9180
caagaatcac tgaggatgac cttcaaaatg aggaactgat cacggaacag atggctcccc    9240
accacaagat cctagccaaa gccatttca aactaaccta tcaaaacaaa gtggtgaaag    9300
tcctcagacc cacaccgaga ggagcggtga tggatatcat atccaggaaa gaccaaagag    9360
gtagtggaca agttggaaca tatggttga acacattcac caacatgaa gttcaactca    9420 tccgccaaat ggaagctgaa ggagtcatca cacaagatga catgcagaac ccaaaagggt    9480
tgaaagaaag agttgagaaa tggctgaaag agtgtggtgt cgacaggtta aagaggatgg    9540
caatcagtgg agacgattgc gtggtgaagc ccctagatga gaggtttggc acttccctcc    9600
tcttcttgaa cgacatggga aaggtgagga agacattcc gcagtgggaa ccatctaagg    9660
gatggaaaaa ctggcaagag gttccttttt gctcccacca ctttcacaag atctttatga    9720
aggatggccg ctcactagtt gttccatgta gaaaccagga tgaactgata gggagagcca    9780
gaatctcgca gggagctgga tggagcttaa gagaaacagc ctgcctgggc aaagcttacg    9840
cccagatgtg gtcgcttatg tacttccaca gaagggatct gcgtttagcc tccatggcca    9900
tatgctcagc agttccaacg gaatggtttc caacaagcag aacaacatgg tcaatccacg    9960
ctcatcacca gtggatgacc actgaagata tgctcaaagt gtggaacaga gtgtggatag   10020
aagacaaccc taatatgact gacaagactc cagtccattc gtgggaagat ataccttacc   10080
tagggaaaag agaggattg tggtgtggat ccctgattgg actttcttcc agagccacct   10140
gggcgaagaa cattcacacg ccataaccc aggtcaggaa cctgatcgga aaagaggaat   10200
acgtggatta catgccagta atgaaaagat acagtgctcc ttcagagagt gaaggagttc   10260
tgtaattacc aacaacaaac accaaaggct attgaagtca ggccacttgt gccacggttt   10320
gagcaaaccg tgctgcctgt agctccgcca ataatgggag cgtaataat ccccaggag    10380 gccatgcgcc acggaagctg tacgcgtggc atattggact agcggttaga ggagacccct   10440
cccatcactg acaaaacgca gcaaaagggg ccccgaagcc aggaggaagc tgtactcctg   10500
gtggaaggac tagaggttag aggagacccc cccaacacaa aaacagcata ttgacgctgg   10560
gaaagaccag agatcctgct gtctctgcaa catcaatcca ggcacagagc gccgcaagat   10620
ggattggtgt tgttgatcca acaggttct                                     10649
```

<210> SEQ ID NO 2
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 2

```
aaaccgtgct gcctgtagct                                                  20
```

```
<210> SEQ ID NO 3
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 3
ggtctcctct aaccgctagt cca                                              23

<210> SEQ ID NO 4
<211> LENGTH: 17
<212> TYPE: DNA
<213> ORGANISM: Artificial Sequence
<220> FEATURE:
<223> OTHER INFORMATION: Synthetic polynucleotide

<400> SEQUENCE: 4
cggaagctgt acgcgtg                                                     17

<210> SEQ ID NO 5
<211> LENGTH: 113
<212> TYPE: DNA
<213> ORGANISM: Dengue virus type 4 strain 814669

<400> SEQUENCE: 5
aaaccgtgct gcctgtagct ccgccaataa tgggaggcgt aataatcccc agggaggcca      60
tgcgccacgg aagctgtacg cgtggcatat tggactagcg gttagaggag acc            113
```

DETECTION OF PARTICLE-CONTAINED REVERSE TRANSCRIPTASE ACTIVITY

RELATED APPLICATION

This application claims priority to and benefit of U.S. Provisional Application No. 62/104,252, filed Jan. 16, 2015. The contents of the aforementioned patent application are herein incorporated by reference in their entireties.

SEQUENCE LISTING

The instant application contains a Sequence Listing which has been submitted in ASCII format via EFS-Web and is hereby incorporated by reference in its entirety. Said ASCII copy, created on Jan. 13, 2016, is named LIGO-02701WO_ST25.txt and is 15,131 bytes in size.

BACKGROUND OF THE INVENTION

Retroviruses are important infectious agents in humans and animals and are responsible for a large number of diseases. A retrovirus may be passed to a subject via contact with a biological sample, e.g., an organ transplant, blood transfusion, and vaccine. Reverse transcriptase (RT) activity is a hallmark of retroviruses and therefore its presence in a biological sample can indicate the presence of a retrovirus particle in the sample.

Cell lines are commonly used for the propagation of recombinant viruses for production of biological products, e.g., vaccines. Such cell lines, which often contain integrated retrovirus-like elements, release RT following cell lysis. Therefore, when a biological product obtained from such a cell line has RT activity, it is unclear whether the RT activity is due to RT released by the cell or due to contamination of the biological product by a viral particle that contains RT; it is import to be able to distinguish between virus particle-contained and free RT activity since the presence of free RT in a biological product is of less significance than the presence of an intact retrovirus particle.

Accordingly, there is an unmet need for methods and kits capable of identifying RT activity in a sample that is due to a virus particle contaminant.

SUMMARY OF THE INVENTION

Provided herein are methods and kits for detecting in a sample the presence of a virus particle or a virus-like particle that has reverse transcriptase activity and methods for preparing a retroviral contaminant-free substance.

An aspect of the present invention is a method for detecting the presence of a virus particle in a sample of a Virus-like Particle (VLP) drug substance comprising a step of performing PCR-based reverse transcriptase (PBRT) on a sample of the VLP drug substance that has been treated with a protease.

Another aspect of the present invention relates to a method for detecting the presence of virus particle-contained reverse transcriptase activity in a test sample. The method includes the steps of: (1) adding a protease to the test sample and incubating the resultant solution under conditions that allow the protease to digest any soluble reverse transcriptase present in the resultant solution, thereby producing a digested solution; (2) inactivating the protease in the digested solution, thereby producing an inactivated protease solution; (3) adding a detergent in an amount that is sufficient to disrupt an intact virus particle, thereby producing a detergent-containing solution; (4) adding to the detergent-containing solution or to a fraction of the detergent-containing solution an isolated RNA molecule, a first primer that hybridizes to a nucleic acid sequence corresponding to a first part of the isolated RNA molecule, a second primer that hybridizes to the complement of a second part of the isolated RNA molecule, and a DNA polymerase, thereby preparing a PCR-based reverse transcriptase (PBRT) assay solution; (5) incubating the PBRT assay solution under conditions that allow a reverse transcription product to be synthesized from the isolated RNA molecule and a PCR-amplified product from the reverse transcription product if a virus particle-contained reverse transcriptase is present in the test sample; and (6) identifying the PCR-amplified product, thereby detecting the presence of the virus particle-contained reverse transcriptase in the test sample. An isolated nucleic acid probe which hybridizes to the nucleic acid sequence corresponding to the isolated RNA molecule may be added during or prior to step (4).

In the above aspect, when the isolated RNA molecule is added in step (4), substantially no DNA template for the isolated RNA molecule is concurrently added. To ensure this, a DNase may be added to the isolated RNA molecule prior to step (4); if added, the DNase is inactivated prior to step (4). Step (4) of the above aspect may further include adding one or more of dNTPs, a reaction buffer, water, $Mg^{2+}$, and $Mn^{2+}$. The DNA polymerase can be Taq Polymerase, a high-fidelity DNA polymerase, or another polymerase known in the art. In some embodiments, a detergent is added during step (1) of the above aspect in an amount that is insufficient to disrupt an intact virus particle.

Some embodiments of the above aspect include a step of concentrating the inactivated protease solution prior to step (3), e.g., by one or more of centrifugation, dialysis, precipitation, or passing through a column. For example, this step may involve subjecting the inactivated protease solution to high speed centrifugation through a sucrose cushion.

In embodiments of the above aspect, at least one sample is obtained and processed according to steps (1) to (6), (2) to (6), (3) to (6), or (4) to (6). In embodiments, positive control samples comprising a soluble reverse transcriptase, e.g., a recombinant reverse transcriptase (e.g., Avian Myeloblastosis virus αβ holoenzyme (AMV RT)), is obtained and processed according to steps (1) to (6), (2) to (6), (3) to (6), or (4) to (6); these positive control samples may include the test sample. In embodiments, positive control samples to which has been added a particle that contains a reverse transcriptase, e.g., a murine leukemia virus (MLV) particle, is obtained and processed according to steps (1) to (6), (2) to (6), (3) to (6), or (4) to (6); these positive control samples may include the test sample. In embodiments, at least one sample is obtained and processed according to steps (1) to (6), (2) to (6), (3) to (6), or (4) to (6) but without adding an isolated RNA molecule in step (4), thereby producing a negative control sample(s); these negative control samples may include the test sample.

In yet another aspect of the present invention is a method for detecting the presence of an RT-containing virus particle in a sample comprising a step of performing PCR-based reverse transcriptase (PBRT) on the sample that has been treated with a protease.

In another aspect of the present invention relates to a method for detecting the presence of an RT-containing virus particle in a Virus-like Particle (VLP) drug substance. The method includes steps of: (1) obtaining a sample of the VLP drug substance; (2) diluting the sample in Proteinase K buffer which is supplemented with Triton X-100 detergent (in an amount that is insufficient to disrupt an intact virus particle) thereby obtaining a diluted sample; (3) adding Proteinase K to the diluted sample and incubating the resultant solution under conditions that allow the Proteinase K to digest any soluble reverse transcriptase present in the resultant solution but not to digest all reverse transcriptase contained in virus particles, thereby producing a digested solution; (4) inactivating the Proteinase K in the digested solution by addition of phenylmethylsulfonyl fluoride (PMSF), thereby producing an inactivated protease solution; (5) centrifuging the inactivated protease solution by high speed centrifugation through a sucrose cushion, thereby producing a concentrated solution; (6) adding a detergent in an amount that is sufficient to disrupt an intact virus particle, thereby producing a detergent-containing concentrated solution; (7) adding to the detergent-containing concentrated solution or to a fraction of the detergent-containing concentrated solution an isolated RNA molecule, a first primer that hybridizes to a 5' end of a nucleic acid sequence corresponding to the isolated RNA molecule, a second primer that hybridizes to the 3' end of the nucleic acid sequence corresponding to the isolated RNA molecule, an isolated nucleic acid probe which hybridizes to the nucleic acid sequence corresponding to the isolated RNA molecule, and a DNA polymerase, thereby preparing a PCR-based reverse transcriptase (PBRT) assay solution; (8) incubating the PBRT assay solution under conditions that allow a reverse transcription product to be synthesized from the isolated RNA molecule and a PCR-amplified product from the reverse transcription product if a virus particle-protected and released reverse transcriptase is present in the PBRT assay solution; and (9) identifying the PCR-amplified product, thereby detecting the presence of the RT-containing virus particle in the VLP drug substance.

Another aspect of the present invention is a retroviral contaminant-free Virus-like Particle (VLP) drug substance. This substance is identified by a method of an above aspect including its embodiments.

An aspect of the present invention relates to a method for detecting the presence of virus particle-contained reverse transcriptase activity in a test sample. The method includes steps of: (1) adding a protease to the test sample and incubating the resultant solution under conditions that allow the protease to digest any soluble reverse transcriptase present in the resultant solution, thereby producing a digested solution; (2) inactivating the protease in the digested solution, thereby producing an inactivated protease solution; (3) adding a detergent in an amount that is sufficient to disrupt an intact enveloped virus particle, thereby producing a detergent-containing solution; (4) adding to the detergent-containing solution or to a fraction of the detergent-containing solution an isolated RNA molecule, a first primer that hybridizes to a nucleic acid sequence corresponding to a first part of the isolated RNA molecule, a second primer that hybridizes to the complement of a second part of the isolated RNA molecule, and a DNA polymerase, thereby preparing a PCR-based reverse transcriptase (PBRT) assay solution; (5) incubating the PBRT assay solution under conditions that allow a reverse transcription product to be synthesized from the isolated RNA molecule and a PCR-amplified product from the reverse transcription product if a virus particle-protected and released reverse transcriptase is present in the PBRT assay solution; and (6) identifying the PCR-amplified product, thereby detecting the presence of the virus particle-contained reverse transcriptase in the test sample. An isolated nucleic acid probe which hybridizes to the nucleic acid sequence corresponding to the isolated RNA molecule may be added during or prior to step (4).

In some embodiments, a detergent is added during step (1) in the above aspect of the present invention in an amount that is insufficient to disrupt an intact enveloped virus particle such that the detergent concentration is less than about 0.002%. In some embodiments, a detergent is added during step (3) such that the detergent concentration in the detergent-containing solution or in the PBRT assay solution is between about 0.1% and 0.3%.

Another aspect of the present invention relates to a method for detecting the presence of an enveloped virus particle in a Virus-like Particle (VLP) drug substance. The method includes steps of: (1) obtaining a sample of the VLP drug substance; (2) diluting the sample in Proteinase K buffer which is supplemented with Triton X-100 detergent (in an amount that is insufficient to disrupt an intact enveloped virus particle) thereby obtaining a diluted sample; (3) adding Proteinase K to the diluted sample and incubating the resultant solution under conditions that allow the Proteinase K to digest any soluble reverse transcriptase present in the resultant solution but not to digest all reverse transcriptase contained in enveloped virus particles, thereby producing a digested solution; (4) inactivating the Proteinase K in the digested solution by addition of Phenylmethylsulfonyl fluoride (PMSF), thereby producing an inactivated protease solution; (5) centrifuging the inactivated protease solution by high speed centrifugation through a sucrose cushion, thereby producing a concentrated solution; (6) adding a detergent in an amount that is sufficient to disrupt an intact virus particle, thereby producing a detergent-containing concentrated solution; (7) adding to the detergent-containing concentrated solution or to a fraction of the detergent-containing concentrated solution an isolated RNA molecule, a first primer that hybridizes to a 5' end of a nucleic acid sequence corresponding to the isolated RNA molecule, a second primer that hybridizes to the 3' end of a nucleic acid corresponding to the isolated RNA molecule, an isolated nucleic acid probe which hybridizes to a nucleic acid corresponding to the isolated RNA molecule, and a DNA polymerase, thereby preparing a PCR-based reverse transcriptase (PBRT) assay solution; (8) incubating the PBRT assay solution under conditions that allow a reverse transcription product to be synthesized from the isolated RNA molecule and a PCR-amplified product from the reverse transcription product if an enveloped virus particle-released reverse transcriptase is present in the PBRT assay solution; and (9) identifying the PCR-amplified product, thereby detecting the presence of the virus particle in the VLP drug substance.

In some embodiments, Triton X-100 is added during step (2) in the above aspect of the present invention such that the detergent concentration is less than about 0.002%. In some embodiments, a detergent is added during step (6) such that the detergent concentration in the detergent-containing concentrated solution or in the PBRT assay solution is between about 0.1% and 0.3%.

Another aspect of the present invention is a method for detecting the presence of a virus particle in a sample comprising a step of performing PCR-based reverse transcriptase (PBRT) on the sample that has been treated with a protease.

Another aspect of the present invention is a method for detecting the presence of an enveloped virus particle containing reverse transcriptase in a sample of a Virus-like Particle (VLP) drug substance comprising a step of performing PCR-based reverse transcriptase (PBRT) on a sample of the VLP drug substance that has been treated with a protease.

The invention includes kits for performing a method of an above aspect including its embodiments. The kits include instructions for use.

Another aspect of the present invention is a retroviral contaminant-free Virus-like Particle (VLP) drug substance. This substance is identified by a method of an above aspect including its embodiments.

In some embodiments, an isolated nucleic acid probe, e.g., having a detectable label, is used which hybridizes to a nucleic acid sequence corresponding to the isolated RNA molecule is added to the inactivated protease solution.

In some embodiments, a test sample is diluted with a buffer, e.g., about one- to about 20-fold (e.g., about 10-fold).

In some embodiments, the detergent is Triton X-100.

In some embodiments, the protease is Proteinase K.

In some embodiments, the protease inhibitor is PMSF.

In some embodiments, the test sample is a Virus-like Particle (VLP) drug substance, e.g., a norovirus (e.g., Norwalk virus) VLP drug substance.

In some embodiments, the isolated RNA molecule is an in vitro-transcribed RNA molecule.

In some embodiments along with the DNA polymerase is added one or more of dNTPs, a reaction buffer, water, $Mg^{2+}$, and $Mn^{2+}$. The DNA polymerase can be Taq Polymerase, a high-fidelity DNA polymerase, or another polymerase known in the art.

In some embodiments, the isolated RNA molecule is at least about 95% identical to a fragment of Dengue virus type 4 genome which has the sequence of SEQ ID NO: 1. The isolated RNA molecule can be at least about 95% identical to the sequence of SEQ ID NO: 5. The first primer may include the sequence of SEQ ID NO: 3 and the second primer may include the sequence of SEQ ID NO: 2. The isolated nucleic acid probe may include the sequence of SEQ ID NO: 4.

Exemplary detergents include Brij-35, Brij-58, CHAPS, CHAPSO, n-Dodecyl-beta-D-Maltoside, NP-40, Octyl glucoside, Octyl thioglucoside, SDS, Sodium Deoxycholate, Triton X-100, Triton X-114, Tween 20, or Tween 80. Preferably, the detergent is Triton X-100.

Examples of a protease includes but is not limited to bromelain, caspase, cathepsins, chymotrypsin, elastase, endoproteinase AspN, endoproteinase GluC, enterokinase (enteropeptidase), Factor Xa, furin, papain, pepsin, Proteinase K, subtilisin, thrombin, or trypsin. Preferably, the protease is Proteinase K. The step of inactivating the protease includes adding one or more protease inhibitors, for example AEBSF-HCl, Aprotinin, Bestatin, E-64, EDTA, Leupeptin, Pepstatin A, and/or Phenylmethylsulfonyl fluoride (PMSF). Preferably, the protease inhibitor is PMSF.

Examples of the detectable label includes but is not limited to biotin, a colloidal particle, digoxigenin, an electron-dense reagent, an enzyme, a fluorescent dye, hapten, a magnetic bead, a metallic bead, and a radioactive isotope. Preferably, the detectable label is a florescent dye. Examples of the florescent dye include 6-FAM, ABY®, Acridine, Alexa Fluor 488, Alexa Fluor 532, Alexa Fluor 594, Alexa Fluor 633, Alexa Fluor 647, BioSearch Blue, Coumarin, Cy® 3, Cy® 3.5, Cy® 5, Cy® 5.5, FAM™, FITC®, GPF (and variants thereof), HEX™, JOE™, JUN®, Marina Blue, NED™, Oregon Green 488, Oregon Green 500, Oregon Green 514, Pacific Blue, PET®, Pulsar®, Quasar® 570, Quasar® 670, Quasar® 705, Rhodamine Green, Rhodamine Red, ROX™, SYBR® Green, TAMRA™, TET™, Texas Red®, TRITC, and VIC®.

The invention includes kits for performing a method of an above aspect including its embodiments. The kits include instructions for use.

Any of the above aspects, embodiments, features, or examples can be combined with any other aspect, embodiment, feature, or example.

Other features and advantages of the invention will be apparent from the Detailed Description, the drawings, and the claims.

DETAILED DESCRIPTION OF THE INVENTION

The present invention relates to methods and kits including a highly-sensitive PCR-based reverse transcriptase (PBRT) assay for detecting retrovirus particle contaminants in a sample. The invention relies on the sensitivity of soluble reverse transcriptase (RT) activity to proteinase K digestion and substantially insensitivity of virus particle-contained RT activity; thus, a sample showing RT activity that is sensitive to proteinase K digestion likely does not have a retrovirus contamination whereas a sample showing RT activity that is substantially insensitive to proteinase K digestion likely has retrovirus contamination.

Without being bound by theory, experimental evidence disclosed herein shows that one or more of the following features of the present invention leads to unexpectedly superior results:
1. Dilution of a sample to be tested into a larger volume of buffer, e.g., Proteinase K buffer, in order to dilute out the high concentration of protein-based components in the sample, allows for a more complete proteolytic degradation of RT not contained in virus particles.
2. Addition of a very small amount of detergent, e.g., Triton X-100, during proteolytic digestion, e.g., by Proteinase K, of virus particles helps facilitate complete digestion. Moreover, the amount of detergent used does not diminish virus particle-contained RT activity.
3. Inactivation of the protease, e.g., Proteinase K, by the addition of a protease inhibitor, e.g., PMSF, is performed following the proteolytic digestion step.
4. Collection and concentration, e.g., high speed centrifugation through a sucrose cushion, of viral particles following the inactivation of the protease, is performed in the presence of the protease inhibitor to ensure that protease activity does not persists during the PBRT reaction.

Definitions

As used herein, the terms "virus", "enveloped virus", "virus-particle" are used interchangeably and refer to a structure that in one attribute resembles a virus but which may or may not been demonstrated to be infectious and/or capable of replication. On the other hand, a "virus-like particle (VLP)" refers to a structure that in one attribute resembles a virus but lacks genetic material. Thus, a VLP is not infectious and/or capable of replication; thus, a VLP is not harmful to a subject. However, an immune response is generated when the subject is vaccinated with a VLP as if the immune system has been presented with a virus.

Examples of Human retroviruses include but are not limited to HIV-1, HIV-2, HTLV-I, and HTLV-II; simian retroviruses include but are not limited to SIV-1 and SIV-2;

other mammalian retroviruses include but are not limited to MLV, FeLV, BLV, and MMTV; and bird retroviruses include but are not limited to ALV and ASV.

Any virus, e.g., retrovirus, which comprises RT can be detected by the present methods and kits.

As used herein, a sample is any sample (e.g., a test sample) that is suspected of containing a virus particle, e.g., as a contaminant. The sample may be a protein solution, a peptide solution, a salt solution, an intravenous (IV) solution, a drug substance, a culture medium, a cell suspension, a suspension comprising an explanted tissue from a subject (e.g., a tissue biopsy or an organ), a blood product, a biological product, an antibody-containing solution (e.g., monoclonal antibody), a vaccine (e.g., an inactivated viral vaccine and a live virus vaccine), or VLP preparation.

A "biological product," as used herein, refers to a product or material that is produced by a cell or organism. The biological product may be a natural product of the organism, or may be produced by an organism that has been altered in some way such that it produces the biological product. Examples of biological products include, but are not limited to, vaccines, antibodies (e.g., monoclonal antibodies), therapeutic proteins, viruses (e.g., recombinant viruses for gene therapy such as, for example, adenovirus, vaccinia virus, pox virus, adeno-associated virus, and herpes virus), enzymes, growth factors, polysactharides, nucleic acids including DNA and RNA, and particles (e.g., virus-like particles). Other non-limiting examples of a biological product include blood (and a blood component), semen, urine, saliva, sputum, and cerebrospinal fluid obtained from a subject. Examples of a blood component include whole blood, serum, plasma, and platelets.

The subject may be from a mammal. The mammal can be a human or a non-human mammal, such as primate, mouse, rat, dog, cat, cow, horse, goat, camel, ox, buffalo, sheep, or pig. The subject can also be a bird or fowl. In embodiments, the mammal is a human.

The term "drug substance", as used herein, refers to the material that contains a therapeutic drug and that is used to formulate, along with excipients, a pharmaceutical composition or drug product.

The terms "isolated", "purified", or "biologically pure" refer to material that is free to varying degrees from components which normally accompany it as found in its native state. "Isolate" denotes a degree of separation from original source or surroundings. "Purify" denotes a degree of separation that is higher than isolation. An isolated product can be obtained from a natural source or can be synthetically obtained; for example, a nucleic acid molecule can be obtained from a cell expressing a gene or coding sequence (i.e., in vitro) and/or can be obtained from a machine that synthesizes the molecule. In other words, a nucleic acid used herein can be naturally-produced or synthetically-produced.

As used herein, the term "primer" refers to a string of linked nucleotide residues comprising a sufficient number of residues to be used in a PCR reaction or in a reverse transcription reaction. A primer may be used to amplify, copy, reverse-transcribe, confirm, or reveal the presence of an identical, similar, or complementary DNA or RNA in a sample. As used herein, the term "probe" refers to a nucleic acid sequence used in the detection of identical, similar, or complementary nucleic acid sequences. A primer can be used to bind to RNA, DNA, or cDNA.

As used herein, a sample is "substantially free" of a virus particle means that the sample does not comprise a detectable level of the virus particle as measured by a PCR or RT-PCR assay or the like.

In some embodiments, the methods and kits described herein utilize enzymes to degrade RNA, such as ribonucleases (RNases). RNases are nucleases that degrade RNA. In some embodiments, RNases provide a thorough means to degrade a non-encapsulated RNA that might otherwise be resistant to degradation due to aggregation. RNases can be endoribonucleases such as RNase A, RNase H, RNase III, RNase I, and others; or exoribonucleases such as RNase II, RNase R, exoribunuclease I, or others. Ribonuclease A (RNase A) is a pancreatic ribonuclease often used in research, and specifically cleaves single-stranded RNA.

The term "DNase" refers to an enzyme that degrades DNA. Any DNase can be used in aspects of the invention. A wide variety of DNases are known and can be categorized including but not limited to DNase I, DNase II, DNase III, DNase IV, DNase V, DNase VI, DNase VII, and DNase VIII.

The term "% identical" as in "95% identical" or "at least about 95% identical" is determined by comparing two optimally aligned sequences over a comparison window, wherein the portion of the polynucleotide sequence in the comparison window may comprise additions or deletions (i.e., gaps) as compared to the reference sequence, which does not comprise additions or deletions, for optimal alignment of the two sequences. The percentage is calculated by determining the number of positions at which the identical nucleotides occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acid sequences, refer to two or more sequences or subsequences that are the same sequences. Sequences are "substantially identical" if two sequences have a specified percentage of nucleotides that are the same (i.e., 60% identity, optionally 65%, 70%, 75%, 80%, 85%, 90%, or 95% identity over a specified region, or, when not specified, over the entire sequence), when compared and aligned for maximum correspondence over a comparison window, designated region as measured using one of the following sequence comparison algorithms or by manual alignment and visual inspection, or across the entire sequence where not indicated Unless specifically stated or obvious from context, as used herein, the term "about", is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Throughout the description, where compositions are described as having, including, or comprising specific components, it is contemplated that compositions also consist essentially of, or consist of, the recited components. Similarly, where methods or processes are described as having, including, or comprising specific process steps, the methods or processes also consist essentially of, or consist of, the recited processing steps. Further, it should be understood that the order of steps or order for performing certain actions is immaterial so long as the invention remains operable. Moreover, two or more steps or actions can be conducted simultaneously.

Unless otherwise defined, all technical and scientific terms used herein have the same meaning as commonly understood by one of ordinary skill in the art to which this invention belongs. In the specification, the singular forms also include the plural unless the context clearly dictates otherwise. Unless specifically stated or obvious from context, as used herein, the terms "a," "an," and "the" are understood to be singular or plural. Unless specifically stated or obvious from context, as used herein, the term "or" is understood to be inclusive.

Methods for isolating, amplifying, or detecting nucleic acids, including methods for detecting and amplifying target RNA or DNA sequences (for example, by polymerase chain reaction (PCR), reverse transcription PCR (RT-PCR), or PCR-based reverse transcriptase (PBRT)) are well known in the art.

One skilled in the art may refer to general reference texts for detailed descriptions of known techniques discussed herein or equivalent techniques. These texts include Ausubel et al., *Current Protocols in Molecular Biology*, John Wiley and Sons, Inc (2005); Sambrook et al., *Molecular Cloning, A Laboratory Manual* (3$^{rd}$ edition), Cold Spring Harbor Press, Cold Spring Harbor, N.Y. (2000); Coligan et al., *Current Protocols in Immunology*, John Wiley & Sons, N.Y.; Enna et al., *Current Protocols in Pharmacology*, John Wiley & Sons, N.Y.; Fingl et al., *The Pharmacological Basis of Therapeutics* (1975), *Remington's Pharmaceutical Sciences*, Mack Publishing Co., Easton, Pa., 18$^{th}$ edition (1990). These texts can, of course, also be referred to in making or using an aspect of the invention.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

In the below examples, the methods of the present invention are used to detect reverse transcriptase (RT) activity in a norovirus virus-like particle (VLP) drug substance that was purified from recombinant baculovirus-infected Sf9 cells, i.e., a cell line used for the propagation of recombinant baculoviruses for production of biologicals and which is known to contain integrated insect retroviral-like elements and to release RT activity following baculovirus-induced lysis. Trace levels of RT activity present in VLP drug substance was demonstrated to be sensitive to proteinase K digestion and therefore not particle-associated. In contrast, Sf9 cell end-of-production-harvest material was shown to contain significant amounts of RT activity; only a very small fraction of this activity was proteinase K-resistant and therefore, this very small fraction is particle-associated. These data demonstrate that the vast majority of RT activity in harvest material is not particle-associated and that there is no evidence for retroviral particle contamination in purified drug substance.

EXAMPLES

Example 1

PCR-Based Reverse Transcriptase (PBRT) Assay can Quantify RT Levels in a Sample Having as Few as Six RT Molecules In order to measure small quantities of RT activity a highly sensitive PCR-based RT (PBRT) assay was required. In separate studies involving the development of arbovirus RT-PCR assays, a particular sequence in the Dengue 4 genome was identified that demonstrates reproducible performance in RT-PCR experiments. In vitro-transcribed RNA containing this sequence as an RNA template was used for the detection of RT activity in a PBRT assay. Table 1 shows primer and probe sequences used in the employed in the Den4 RT-PCR assay.

TABLE 1

| | Sequence (5' to 3') | Fluorophore | Quencher | Nucleotide Position | SEQ ID NO: |
|---|---|---|---|---|---|
| Dengue virus type 4 strain 814669, complete | AF326573 | | | 1-10649 | 1 |
| Den4 Fwd | aaaccgtgctgcctgtagct | | | 10325-10344 | 2 |
| Den4 Rev | ggtctcctctaaccgctagtcca | | | 10415-10437 (rc) | 3 |
| Den4 Probe | cggaagctgtacgcgtg | FAM | MGB-NFQ | 10392-10408 | 4 |
| 113 nt Den 4 sequence | aaaccgtgctgcctgtagctcc gccaataatgggaggcgtaata atccccagggaggccatgcgc cacggaagctgtacgcgtggc atattggactagcggttagagg agacc | | | 10325-10437 | 5 |

A 113 nt synthetic DNA sequence representing the above-mentioned portion of the Den4 genome was cloned into plasmid pcDNA 3.1 between the NotI and KpnI sites. The resulting clone was linearized with PstI. Linearized DNA was used in an in vitro transcription reaction to generate an approximate a 1.5 kb RNA molecule containing the 113 nt Den4 synthetic sequence which served as the template RNA for the PBRT assay.

For the template RNA to be useful in a PBRT assay it is helpful to eliminate all plasmid DNA template used in the in vitro transcription reaction since residual DNA would effectively yield a PCR signal in the absence of added RT. This was achieved by employing multiple rounds of Turbo™ DNase Treatment (Life Technologies™; Carlsbad, Calif., USA) followed by a final purification step employing the RNeasy Mini Kit (Qiagen; Venlo, Limburg, NL). The final purified RNA product showed no evidence of degradation when analyzed by glyoxal agarose gel electrophoresis.

The positive control RT enzyme employed in the PBRT assay was the Avian Myeloblastosis virus αβ holoenzyme of molecular weight 157,000 daltons supplied by Life Sciences, Advanced Technologies, Inc. (St Petersburg, Fla., USA). This is a highly purified enzyme preparation free of nucleases with a specific activity of 62,686 units/mg. A standard curve of this enzyme was established ranging from 0.1 nanounits (nu) to 10,000 nu per µL and 1 µL of each standard curve sample was added to a PBRT standard curve reaction which resulted in a range of 6 molecules to 600,000 molecules of RT in the PBRT standard curve. All PBRT reactions employed 5 ng of Den4 template RNA as well as the Den4 primers and probe and buffer components. Two reactions containing no added RT served as controls for background signals arising from residual DNA in the RNA template preparation. A "no template" control lacking the Den4 RNA was also run. Table 2 shows that when samples are run in triplicate for 40 cycles, a linear RT standard curve is observed with an $R^2$ value of 0.986. The $R^2$ value was slightly less than 0.99 due to a small amount of scatter in the 0.1 nu standard curve triplicate samples (6 molecules of RT per reaction). Importantly, the "No RT" samples exhibited Ct values only slightly less than 40, which demonstrates success in eliminating background signals due to residual DNA.

(MLV) particles. An assay was deemed successful when RT activity due to AMV RT supplementation was eliminated by PK activity whereas RT activity from MLV particle supplementation was protected (i.e., RT activity persisted). It appeared that a crucial part of the assay was the ability to completely inactivate PK activity following PK treatment so that proteolytic activity would not be carried over into the PBRT assay steps and thereby reduce the RT-PCR performances. Also, it was determined that a PK inhibitor must not interfere with the PBRT assay.

It was discovered that a successful method involved one or more of the following steps:
1. Dilution of a sample to be tested into a larger volume of Proteinase K buffer, in order to dilute out the high concentration of virus-like particles in the sample, allowing for a more complete proteolytic degradation of RT not contained in virus particles.
2. Addition of a very small amount of Triton X-100 during Proteinase K digestion of virus particles helps facilitate complete digestion. Moreover, the amount of Triton X-100 used does not diminish virus particle-contained RT activity.
3. Inactivation of the Proteinase K, by the addition of PMSF, is necessary following the proteolytic digestion step.

TABLE 2

| | Sample | | | | | | | | |
|---|---|---|---|---|---|---|---|---|---|
| | 10,000 nu RT | 1000 nu RT | 100 nu RT | 10 nu RT | 1 nu RT | 0.1 nu RT | No RT | No RT | No Template |
| Ct Value | 17.54 | 20.77 | 24.10 | 27.53 | 30.65 | 34.73 | 39.02 | 39.01 | ≥40 |

These data verify the ability of the present method to quantify RT levels down to 0.1 nu or six molecules per sample.

The above-mentioned PBRT assays were run using the TaqMan RNA-to-CT 1-Step Kit (Life Technologies™, catalog numbers 4392653, 4392938, and 4392656) with the exception that the RT enzyme from the kit was not added to the reactions since the assays were being used to detect the presence of contaminating RT or RT associated with the AMV RT and MLV spikes. Cycle times and temperatures were those described by the kit manufacturer.

Example 2

The PBRT Assay can Distinguish Between Particle-Associated and Free RT Activity in Test Samples Proteinase K (PK) was selected as an exemplary protease for distinguishing between particle-contained and free RT enzymatic activity. It was posited that under appropriate conditions PK would effectively eliminate all non-particle-contained RT activity in a given sample whereas the RT activity in intact, enveloped retroviral particles would be protected from proteolytic digestion. Conditions for this methodology were developed using norovirus VLP drug substance samples as a model. As a control for free (non-virus particle-contained) enzymatic activity samples of the VLP drug substance were supplemented with avian myeloblastosis virus (AMV) RT. As a control for RT contained in intact retrovirus particles, samples of the VLP drug substance were supplemented with murine leukemia virus 4. Collection and concentration by high speed centrifugation through a sucrose cushion, of viral particles following the inactivation of Proteinase K should occur in the presence of the PMSF to ensure that Proteinase K activity does not persists during the PBRT reaction.

Example 3

The PBRT Assay can Distinguish in a Test Sample Activity Due to Endogenous RT, Activity Due to Supplemented RT, and Activity Due to Supplemented Virus Particle-Contained RT Three 0.5 mL samples of Norwalk VLP drug substance were analyzed according to the PBRT assay of Example 1. Sample 1 was not supplemented. Samples 2 and 3, which served as positive controls, were supplemented with AMV RT or MLV, respectively. Following supplementation, 25 µL of each sample was set aside to determine baseline RT activities, i.e., prior to proteolytic digestion. The remainder of each sample was subjected to PK digestion, followed by recovery of intact virus particles by high speed centrifugation. Prior to assaying for RT activity, all samples were diluted 1:2 with 2× AMV dilution buffer (a source of non-ionic detergent) to lyse (disrupt) any enveloped particles, thereby ensuring that all RT activity was being measured. The PK digested and set aside samples were assayed for RT activity using the PBRT assay described in Example 1. Data from this experiment are shown in Table 3

TABLE 3

| | Ct Values from PBRT (40 cycles) | | |
| --- | --- | --- | --- |
| | Sample 1 - No supplementation | Sample 2 - supplemented with AMV RT | Sample 3 - supplemented with MLV particles |
| Baseline RT | 33.3 | 17.6 | 18.4 |
| Post-PK and Recovery | 39.7 | 39.4 | 16.5 |
| No RT Control | | 38.5 | |

As shown in Table 3, test sample 1, which was not supplemented, exhibited a small level of baseline RT activity (Ct value=33.3) prior to PK treatment. However, following PK treatment and recovery, the Ct value increased to 39.7, which is similar to "No RT control" levels. These data indicate that the baseline RT activity is not particle associated, is susceptible to PK digestion, and is not recoverable by high speed centrifugation. Sample 2, which was supplemented with AMV RT, behaved as expected in that it exhibited very strong RT baseline activity (Ct=17.6) prior to PK digestion but after PK digestion and high speed centrifugation RT activity returned to "No RT Control" levels. This indicates that both the endogenous and supplemented RT activities were degraded by PK. Similar to sample 2, sample 3, which was supplemented with MLV particles, exhibited strong baseline RT activity (Ct value=18.4). However, unlike sample 2, in sample 3, PK digestion and high speed recovery of intact particles actually resulted in an increase in RT activity (Ct value=16.5) due to concentration of the PK-resistant, intact MLV particles by the centrifugation recovery step.

These data support a premise that small amounts of measurable RT activity is present in Norwalk VLP drug substance which is not particle associated and is susceptible to proteolytic degradation. In other words, this endogenous RT activity is not due to intact retrovirus particle contamination.

The experiments described above were replicated with similar results observed. See, Table 4.

TABLE 4

| | Ct Values from PBRT (40 cycles) | | |
| --- | --- | --- | --- |
| | Sample 1 - No supplementation | Sample 2 - supplemented with AMV RT | Sample 3 - supplemented with MLV particles |
| Baseline RT | 35.5 | 35.5 | 35.5 |
| Post-PK and Recovery | 39.0 | 39.0 | 39.0 |
| No RT Control | | 40.0 | |

In control experiments for the data presented in Tables 3 and 4, every sample tested in the PBRT reactions was also tested following supplementation with AMV RT in order to test for the possibility of protease carry over into the PBRT reactions. In this case every "spiked" sample showed a similarly strong RT signal demonstrating good performance of the PBRT reaction which was indicative of the absence of protease carryover.

Example 4

End of Production Harvest Material Fractions have Greater RT Activity Relative to Earlier Harvest Fractions It has been shown that particle-associated errantivirus RNA sequences are more prevalent in end of production (EOP) harvest material fractions (i.e., baculovirus-lysed Sf9 cells) relative to medium harvested from healthy, non-baculovirus-infected Sf9 cells; it is believed that EOP harvest material fractions contain greater amounts both free and particle-associated RT than medium harvested from healthy Sf9 cells.

EOP harvest test samples were tested as described in Example 3 samples except that the EOP samples were diluted 10-fold in PK buffer; this was because a preliminary experiment demonstrated exceptionally high initial RT levels in EOP test samples, which would hinder distinguishing RT activity among samples. Table 5 shows the results of this experiment.

TABLE 5

| | Ct Values from PBRT (40 cycles) | | |
| --- | --- | --- | --- |
| | EOP Sample 1 - No supplementation | EOP Sample 2 - supplemented with AMV RT | EOP Sample 3 - supplemented with MLV particles |
| Baseline RT | 19.7 | 18.7 | 18.4 |
| Post-PK and Recovery | 30.7 | 30.4 | 19.4 |
| No RT Control | | 39.4 | |

As can be seen in Table 5, EOP Sample 1, the un-supplemented sample, had a strong baseline RT activity. Baseline RT activity for EOP Sample 2, the AMV RT-supplemented sample, was only about two-fold greater. EOP Samples 1 and 2 exhibited essentially identical Ct values as each other following PK digestion and their recovery that fell to within the RT standard curve range, which indicates the presence of a PK-resistant, particle-contained fraction of RT activity in EOP harvest material. On the other hand, EOP Sample 3, the MLV-supplemented sample, showed strong baseline RT activity and activity after PK digestion; this is consistent with the PK-resistant-MLV spike which served as a control for the successful recovery of RT from intact retrovirus particles.

Data from the three EOP samples are consistent with the presence of PK-resistant, particle-contained RT in EOP harvest material. However, the particle-contained RT is clearly a small fraction with respect to the total amount of RT activity in the initial harvest sample since the pre- and post-PK signals differ by over three orders of magnitude when compared to the RT standard curve. This observation is consistent with the absence of detectable particle-associated RT activity in purified drug substance, as described in Example 3. The low level of particle-associated RT activity in harvest material to begin with, coupled with the use of a detergent step in the VLP purification process, are likely important factors leading to the absence of detectable particle-associated RT activity in the final drug substance.

Example 5

Alternative Divalent Cation Test

Data presented in the prior Examples were generated in experiments employing $Mg^{2+}$ ions in the RT-PCR buffer. In order to allow for the possibility of detecting novel RT activity from enzymes requiring $Mn^{2+}$ ions, the drug substance evaluation experiment was repeated with the addition of 3 mM $MnCl_2$ in the RT-PCR master mix buffer. Results of these experiments are shown in Table 6.

TABLE 6

Ct Values from PBRT (40 cycles) (MnCl$_2$ supplementation)

| | EOP Sample 1 - No supplementation | EOP Sample 2 - supplemented with AMV RT | EOP Sample 3 - supplemented with MLV particles |
|---|---|---|---|
| Baseline RT | 40.0 | 29.3 | 25.4 |
| Post-PK and Recovery | 40.0 | 40.0 | 24.5 |
| No RT Control | | 40.0 | |

Table 6 shows that the outcomes are qualitatively similar to the results shown in Tables 3 and 4 with the exception that all of the Ct values were skewed upward Therefore, Mn$^{2+}$ ions did not stimulate the detection of a novel Mn$^{2+}$-dependent RT that might have been present in an as of yet unidentified contaminating retrovirus. RT activity in drug substance and the RT and MLV spikes resulted in the same patterns previously observed.

EQUIVALENTS

The invention can be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A method for detecting the presence of virus particle-contained reverse transcriptase activity in a test sample comprising steps of:
   (1) adding to the test sample a protease and a detergent in an amount that is insufficient to disrupt an intact virus particle and incubating the resultant solution under conditions that allow the protease to digest any soluble reverse transcriptase present in the resultant solution, thereby producing a digested solution;
   (2) inactivating the protease in the digested solution, thereby producing an inactivated protease solution;
   (3) adding a detergent in an amount that is sufficient to disrupt an intact virus particle, thereby producing a detergent-containing solution;
   (4) adding into the detergent-containing solution or into a fraction of the detergent-containing solution (i) an isolated RNA molecule, (ii) a first primer that hybridizes to a nucleic acid sequence corresponding to a first part of the isolated RNA molecule, (iii) a second primer that hybridizes to the complement of a second part of the isolated RNA molecule, and (iv) a DNA polymerase, thereby preparing a PCR-based reverse transcriptase (PBRT) assay solution;
   (5) incubating the PBRT assay solution under conditions that allow a reverse transcription product to be synthesized from the isolated RNA molecule and a PCR-amplified product from the reverse transcription product if a virus particle-contained reverse transcriptase is present in the test sample; and
   (6) identifying the PCR-amplified product, thereby detecting the presence of the virus particle-contained reverse transcriptase in the test sample.

2. The method of claim 1, wherein an isolated nucleic acid probe comprising a detectable label which hybridizes to a nucleic acid sequence corresponding to the isolated RNA molecule is added after step (3) or during step (4).

3. The method of claim 1, wherein the test sample is diluted with a buffer.

4. The method of claim 1, wherein the detergent is added during step (1) such that the detergent concentration in the digested solution is less than about 0.002%.

5. The method of claim 1, wherein the detergent is added during step (3) such that the detergent concentration in the detergent-containing solution or in the PBRT assay solution is between about 0.1% and 0.3%.

6. The method of claim 1, wherein the step of inactivating the protease comprises adding at least one protease inhibitor.

7. The method of claim 1, further comprising a step of concentrating the inactivated protease solution prior to step (3).

8. The method of claim 1, wherein a positive control sample comprising a soluble reverse transcriptase or a particle that contains a reverse transcriptase is obtained and processed according to steps (1) to (6), (2) to (6), (3) to (6), or (4) to (6).

9. The method of claim 8, wherein the positive control sample comprises the test sample.

10. The method of claim 1, wherein a sample is obtained and processed according to steps (1) to (6) but without adding an isolated RNA molecule in step (4), thereby producing a negative control sample.

11. The method of claim 2, wherein the detectable label is selected from the group consisting of biotin, a colloidal particle, digoxigenin, an electron-dense reagent, an enzyme, a fluorescent dye, hapten, a magnetic bead, a metallic bead, and a radioactive isotope.

12. The method of claim 1, wherein the test sample is a Virus-like Particle (VLP) drug substance.

13. The method of claim 12, wherein the VLP drug substance is a norovirus VLP drug substance.

14. The method of claim 13, wherein the norovirus is the Norwalk virus.

15. The method of claim 1, wherein the isolated RNA molecule is at least about 95% identical to a fragment of Dengue virus type 4 genome which has the sequence of SEQ ID NO: 1.

16. The method of claim 15, wherein the isolated RNA molecule is at least about 95% identical to the sequence of SEQ ID NO: 5.

17. The method of claim 1, wherein the first primer comprises the sequence of SEQ ID NO: 3.

18. The method of claim 1, wherein the second primer comprises the sequence of SEQ ID NO: 2.

19. A method for detecting the presence of an enveloped virus particle in a Virus-like Particle (VLP) drug substance comprising steps of:
  (1) obtaining a sample of the VLP drug substance;
  (2) diluting the sample in Proteinase K buffer which is supplemented with Triton X-100 detergent thereby obtaining a diluted sample,
    wherein the Triton X-100 is present in an amount that is insufficient to disrupt an intact virus particle;
  (3) adding Proteinase K to the diluted sample and incubating the resultant solution under conditions that allow the Proteinase K to digest any soluble reverse transcriptase present in the resultant solution but not to digest all reverse transcriptase contained in virus particles, thereby producing a digested solution;
  (4) inactivating the Proteinase K in the digested solution by addition of Phenylmethylsulfonyl fluoride (PMSF), thereby producing an inactivated protease solution;
  (5) centrifuging the inactivated protease solution by high speed centrifugation through a sucrose cushion, thereby producing a concentrated solution;
  (6) adding a detergent in an amount that is sufficient to disrupt an intact virus particle, thereby producing a detergent-containing concentrated solution;
  (7) adding to the detergent-containing concentrated solution or to a fraction of the detergent-containing concentrated solution an isolated RNA molecule, a first primer that hybridizes to a 5' end of a nucleic acid sequence corresponding to the isolated RNA molecule, a second primer that hybridizes to the 3' end of the isolated RNA molecule, an isolated nucleic acid probe which hybridizes to the isolated RNA molecule, and a DNA polymerase, thereby preparing a PCR-based reverse transcriptase (PBRT) assay solution;
  (8) incubating the PBRT assay solution under conditions that allow a reverse transcription product to be synthesized from the isolated RNA molecule and a PCR-amplified product from the reverse transcription product if a virus particle containing a reverse transcriptase is present in the PBRT assay solution; and
  (9) identifying the PCR-amplified product, thereby detecting the presence of the enveloped virus particle in the VLP drug substance.

* * * * *